United States Patent [19]

Morrison et al.

[11] Patent Number: 5,082,789
[45] Date of Patent: Jan. 21, 1992

[54] BISMUTH MOLYBDATE GAS SENSOR

[75] Inventors: Stanley R. Morrison; Norma J. Hykaway, both of Burnaby; William M. Sears, Port Moody; Robert F. Frindt, Vancouver, all of Canada

[73] Assignee: Simon Fraser University, Brunaby, Canada

[21] Appl. No.: 235,369

[22] Filed: Aug. 23, 1988

[51] Int. Cl.$^5$ .................. G01N 31/10; G01N 27/12
[52] U.S. Cl. .................. 436/132; 73/23.31; 422/94; 422/98; 436/131; 436/144; 436/128; 436/141; 436/142; 436/152
[58] Field of Search .......... 422/98, 94; 436/131, 436/132, 144; 73/27 R

[56] References Cited

U.S. PATENT DOCUMENTS 4,587,104  5/1986  Yannopoulos .................. 422/98 X
4,668,635  5/1987  Forster .......................... 422/94 X

OTHER PUBLICATIONS

The Condensed Chemical Dictionary, 8th Ed., Van Nostrand, Reinhold Co., New York, p. 627.
*Thick Film Circuits*, G. V. Flaner & L. S. Phillips, London Butterworths, 1972 pp. 1-9.
Chambers Science & Technology Dictionary, Peter M. B. Walker, Chambers Cambridge Co., Cambridge, p. 899.

*Primary Examiner*—Robert J. Warden
*Assistant Examiner*—Amalia Santiago
*Attorney, Agent, or Firm*—Barrigar & Oyen

[57] ABSTRACT

A bismuth molybdate gas sensor which provides stable sensitivity to gases such as alcohol, ketones, alkenes, and long chain alkanes is disclosed. Sensors comprising a mixture of the $Bi_2Mo_3O_{12}$ and $Bi_2MoO_6$ phases of bismuth molybdate; or, bismuth iron molybdate are particularly effective. The bismuth molybdate mixture; or, the bismuth iron molybdate may be deposited as a thin film on a substrate or may take the form of a sintered powder.

13 Claims, 10 Drawing Sheets

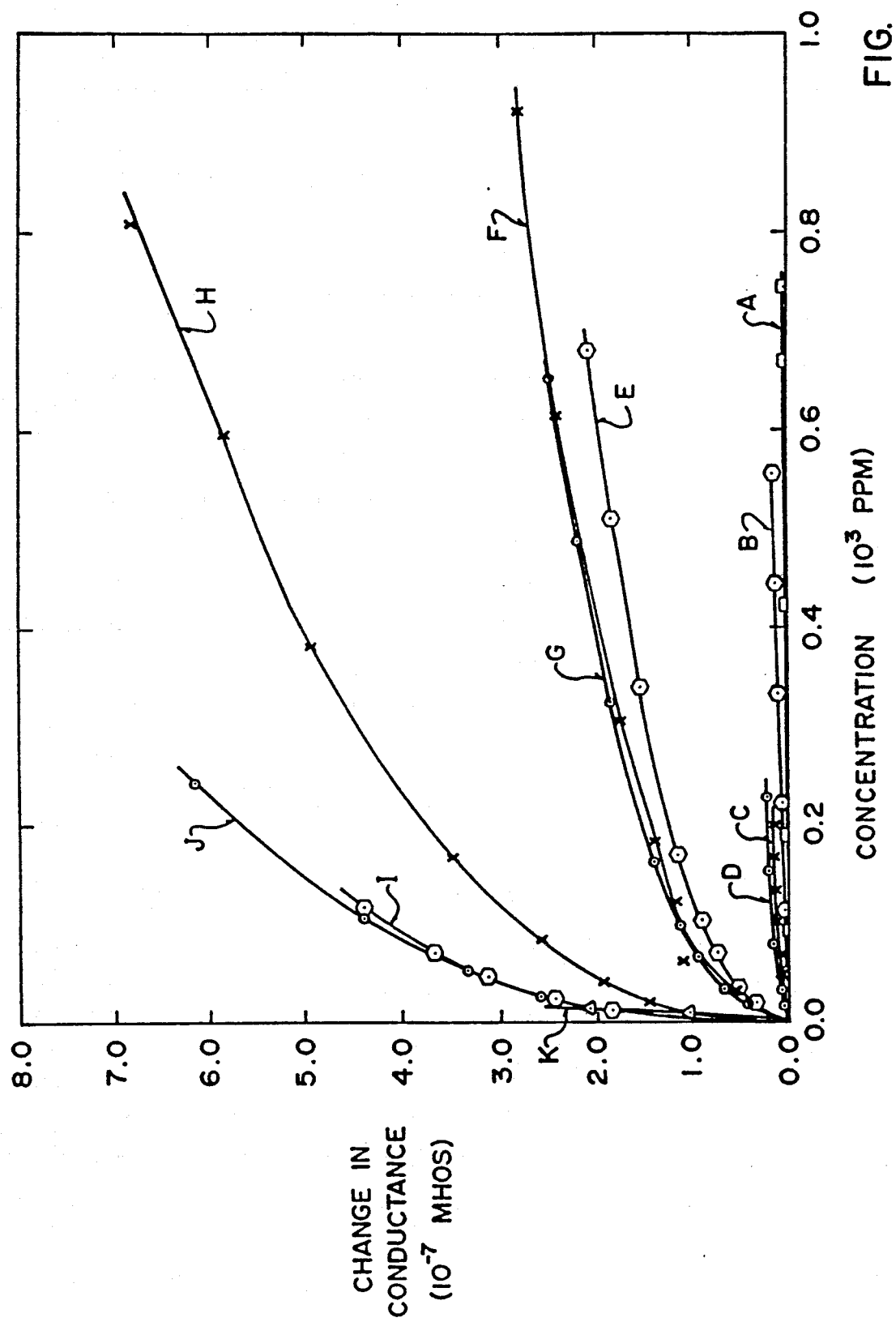

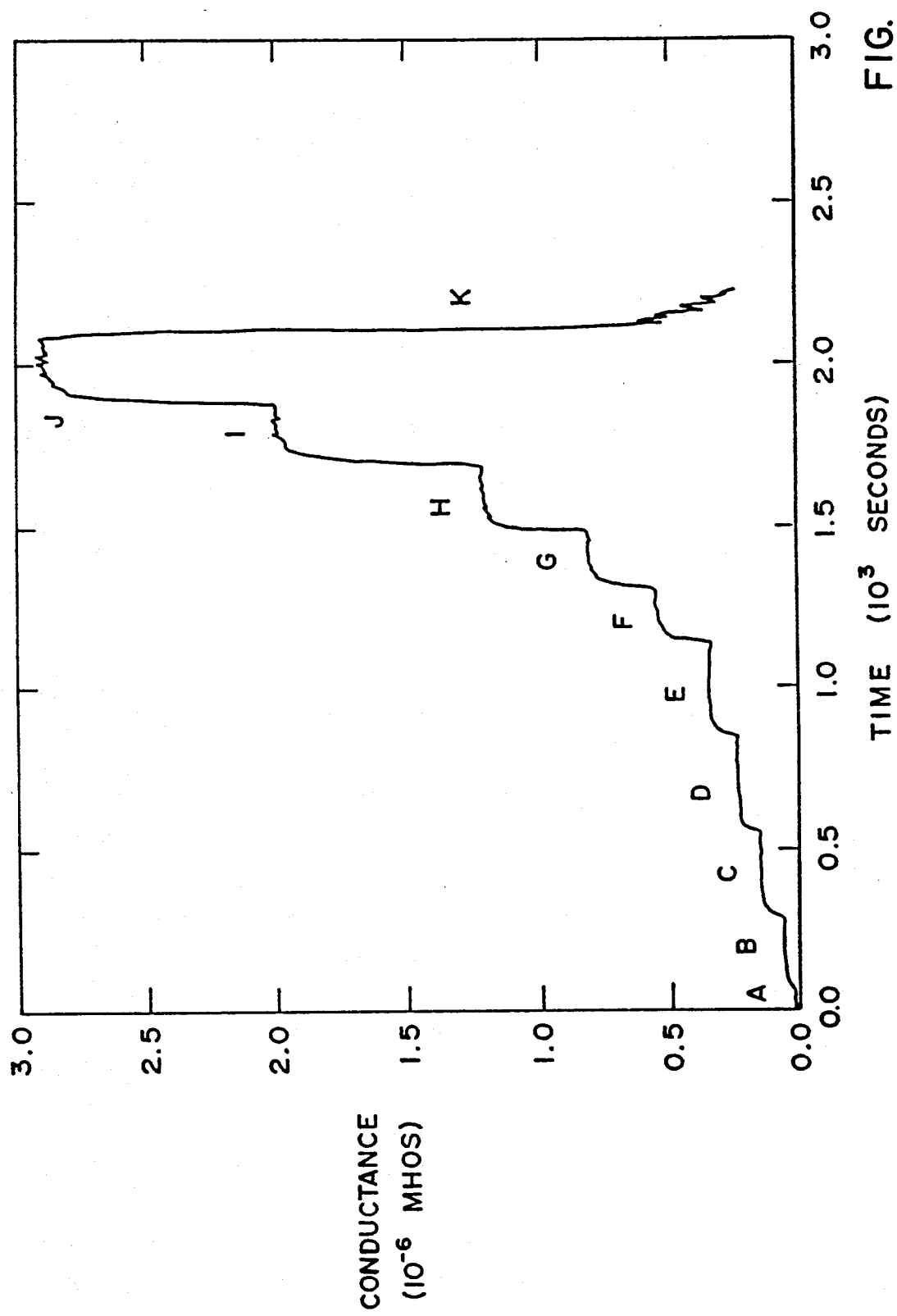

BISMUTH MOLYBDATE GAS SENSOR

FIELD OF THE INVENTION

This invention is directed to novel gas sensors, more particularly novel semiconducting oxide gas sensors.

BACKGROUND OF THE INVENTION

The use of semiconducting oxides as gas sensors, particularly where the oxide is used in a pressed and sintered powder form, has been common for several years. The electrical resistance of such sensors has been found to vary in a predictable manner when the sensor is operated in the presence of a particular gas, or concentration of gas, thus facilitating detection of particular gases or gas concentrations. Prior art semiconductor gas sensors however suffer from lack of stability, lack of reproducibility, and sensitivity to the relative humidity in the atmosphere. The reason for the sensitivity, and to a great extent the reason for the lack of stability and the lack of reproducibility, is believed to be associated with the fact that prior art gas sensors depend on intergranular contacts between powder grains for their sensitivity. For example, in a prior art gas sensor based on tin oxide, the gases in the atmosphere interact at the surface of the tin oxide grain, affecting the intergranular contacts and thus affecting the electrical properties of the sintered powder. Because of the sensitivity of the surface to humidity, and because of the difficulties with reproducibility of intergranular contacts, the sensors have the abovementioned problems.

The inventors have found that bismuth molybdate (a term which is hereafter used to describe an oxide where bismuth and molybdenum are cations of various atomic percentages and oxygen is the anion) can be used as a gas sensor with good sensitivity for certain gases and good reproducibility and stability, and in particular almost zero dependence of the sensor characteristics (the electrical resistivity) on the relative humidity. Bismuth molybdate gas sensors can be particularly useful for the detection of alcohol in the breath, having both substantial sensitivity in the concentration range of interest (200 ppm) and having negligible response to the humidity from the breath. There are certain other organic species that the sensor will detect, as will be described.

The inventors have also found that bismuth iron molybdate ($Bi_3FeMo_2O_{12}$) can be used as a gas sensor in much the same way and with much the same properties as bismuth molybdate. The inventors have also found that the sensitivity and linearity of the bismuth iron molybdate sensor can be improved by mixing with platinum black. These compounds are part of a whole class of catalysts (molybdates) which the inventors expect to have much the same properties.

Although not wanting to be bound by any theory, the inventors believe that the insensitivity of a bismuth molybdate sensor to humidity arises because the changes in electrical resistance exhibited by the bismuth molybdate class of materials, when exposed to gases, are associated with the materials' bulk properties, rather than surface properties (intergranular contacts) as is the case with tin oxide and other such sensors. The resistance is associated with the bulk because lattice oxygen vacancies diffuse extremely rapidly through the semiconductor. This means bulk equilibrium of the catalyst stoichiometry (metal to oxide ratio) with the surrounding gas can be very rapid.

Bismuth molybdate sensors can be used in the form of a thin film of material or as a sintered powder. The thin film form is particularly useful where low sensor power and fast response time is important. In the case of bismuth molybdate which exists as several crystallographic structures the stoichiometry (ratio of bismuth to molybdenum atoms) is found to be important. A mixture of the alpha ($Bi_2Mo_3O_{12}$) and gamma ($Bi_2MoO_6$) phases of bismuth molybdate provides the optimum gas sensitivity.

SUMMARY OF THE INVENTION

The invention provides, in one embodiment, a gas sensor comprising a mixture of the $Bi_2Mo_3O_{12}$ and $Bi_2MoO_6$ phases of bismuth molybdate. In a second embodiment, the invention provides a gas sensor comprising bismuth iron molybdate. The gas to be sensed may be an alcohol, a ketone, an alkene, or a long chain alkane.

Gas sensors constructed in accordance with the second embodiment of the invention may be doped with platinum, silver or palladium to improve their sensitivity to particular gases such as hydrogen or ethanol.

The bismuth molybdate mixture; or, the bismuth iron molybdate comprising the gas sensor, may be deposited as a thin film on a substrate; or, may take the form of a sintered powder.

The invention also provides a method of measuring gas concentration comprising the steps of exposing the gas to a sensor constructed in accordance with either the first or second embodiments of the invention and then measuring the electrical resistance of the sensor. The sensor is preferably heated to an operating temperature of about 340 degrees celsius.

BRIEF DESCRIPTION OF THE DRAWINGS

FIG. 2 is a graph on which gas concentration (in thousands of parts per million) is plotted as the abscissa, versus change in conductance (in $10^{-7}$ mhos) as the ordinate for an evaporated film of bismuth molybdate upon exposure to several representative gases.

FIG. 6(a) is a graph on which time (in thousands of seconds) is plotted as the abscissa, versus conductance (in $10^{-6}$ mhos) as the ordinate for a bismuth molybdate sensor constructed in accordance with the invention, and exposed to various concentrations of ethanol vapor.

DETAILED DESCRIPTION OF THE PREFERRED EMBODIMENTS

Figure 1A:
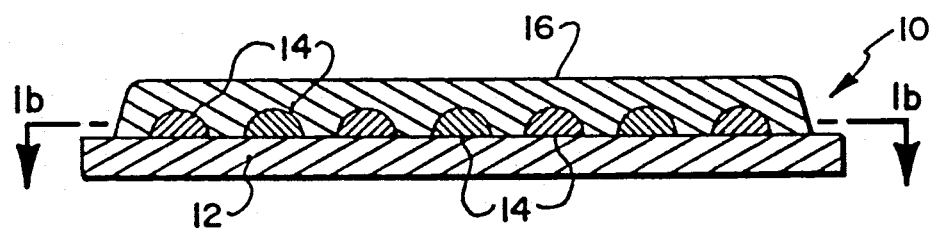
FIGS. 1(a) and 1(b) are, respectively, side and top cross-sectional views of an evaporated layer of bismuth molybdate on a quartz substrate with gold contacts.

The inventors have discovered that the bismuth molybdate class of sensors provides significant advantages over other materials reported in the literature insofar as use as a gas sensor is concerned. These advantages are believed to arise because of the fact that, with the high oxygen vacancy mobility in the material, we are dealing with a bulk resistance change rather than with the surface resistance change reported for other semiconducting oxide gas sensors.

Bismuth molybdate can be formed from solution by co-precipitation of bismuth and molybdenum oxide from bismuth nitrate and ammonium heptamolybdate. After calcining, a thin film can be produced by evaporation, using the bismuth molybdate powder as source. Other thin film techniques well known in the art, such as sputtering, can be used. The crystal structure of the material depends on the stoichiometry of the bismuth and molybdenum used. Three structures are known in the literature as the alpha ($Bi_2Mo_3O_{12}$), beta ($Bi_2Mo_2O_9$) and gamma ($Bi_2MoO_6$) phases of bismuth molybdate. The inventors have found that optimum gas sensitivity is attained with bismuth molybdate films that consist of a mixture of the alpha and gamma phases.

Bismuth iron molybdate is prepared in a similar manner, namely by the co-precipitation of bismuth nitrate, iron nitrate and ammonium heptamolybdate. This compound has only one stable stoichiometry ($Bi_3FeMo_2O_{12}$) although mixed phases with bismuth molybdate or other binary or simple oxides are possible. Evaporated films of $Bi_3FeMo_2O_{12}$ cannot be readily produced because the iron in this compound cannot be readily co-evaporated. However, it can be pressed into pellets which are much stronger than those of bismuth molybdate. In pellet form surface active powders (catalysts) can be added.

Bismuth molybdate and bismuth iron molybdate are well known as partial oxidation catalysts, for example, in the oxidation of propene to acrolein. In studies in the catalytic literature there is substantial evidence that the catalytic activity arises because the organic material removes lattice oxygen and the oxide vacancies diffuse rapidly away from the surface. Because the oxygen vacancies are donors the conductivity of the catalyst rises rapidly as the oxygen is extracted. This electrical effect has no particular interest in catalysis but is of great interest in gas sensing.

In normal operation in air there are two competing reactions:

$$R + O_L \rightarrow RO + e^- + V_0^+ \tag{1}$$

$$1/2 O_2 + V_0^+ + e^- \rightarrow O_L \tag{2}$$

where $V_0^+$ is an ionized oxygen vacancy, the electron $e^-$ going into the conduction band. $O_L$ is a lattice oxygen and R a reducing agent such as ethanol or CO. The reactions are only intended to be examples, to illustrate the general processes of oxygen removal by a reducing agent and restoration by gaseous oxygen. Without the reducing agent in the atmosphere the density of oxygen vacancies is very low so that the conductivity of the bismuth molybdate is very low. When reaction 1 begins to occur due to the presence of the reducing agent the oxygen vacancy density and the electron density in the bulk increase rapidly resulting in a high conductivity, and this result allows the reducing agent to be detected by a conductivity measurement.

Because the bismuth molybdates are a common catalyst for the oxidation of propene, many bismuth to molybdenum ratios were tested to find a propene sensor. Although the bismuth molybdate material was found to be a good sensor for propene (compared to propane) it was found to be even better for alcohols and ketones as shown in Tables 1 and 2. In particular it is an excellent sensor for ethanol. As mentioned earlier, another desirable feature manifested itself, namely insensitivity to relative humidity.

TABLE 1

| The Selectivity of Bismuth Iron Molybdate Gas Sensing Pellets | | | | | | | | | |
|---|---|---|---|---|---|---|---|---|---|
| | sintered at 400° C. | | | sintered at 500° C. | | | with Pt black | | |
| Reducing Gas | $G_0$ | $G_{200}$ | slope | $G_0$ | $G_{200}$ | slope | $G_0$ | $G_{200}$ | slope |
| CO | 0.040 | 0.071 | 0.54 | — | — | — | — | — | — |
| $H_2$ | 0.048 | 0.070 | — | 0.51 | 1.07 | — | 0.017 | 0.043 | — |
| methane | 0.035 | 0.009 | — | — | — | — | — | — | — |
| propane | 0.042 | 0.059 | — | 0.51 | 0.41 | — | 0.017 | 0.042 | 0.78 |
| propene | 0.030 | 0.61 | 0.61 | — | — | — | 0.018 | 0.51 | 0.71 |
| hexane | 0.029 | 0.59 | 0.51 | — | — | — | 0.031 | 1.34 | 0.74 |
| methanol | 0.032 | 0.97 | 0.56 | 0.43 | 5.50 | 0.55 | 0.016 | 0.31 | 0.88 |
| ethanol | 0.044 | 1.38 | 0.55 | 0.23 | 7.59 | 0.39 | 0.017 | 1.16 | 0.88 |
| 2-propanol | 0.067 | 0.86 | 0.55 | — | — | — | 0.017 | 0.90 | 0.79 |
| acetone | 0.068 | 1.47 | 0.54 | 0.49 | 8.58 | 0.42 | 0.013 | 1.68 | 0.87 |
| 3-pentanone | 0.028 | 1.42 | 0.55 | — | — | — | 0.028 | 1.95 | 0.77 |
| | | | | sintered at 600° C. | | | with Ag added | | |
| $H_2$ | | | | — | — | — | 0.033 | 0.37 | 0.70 |
| ethanol | | | | 0.71 | 4.70 | 0.29 | 0.028 | 0.29 | 0.75 |

TABLE 1-continued

The Selectivity of Bismuth Iron Molybdate Gas Sensing Pellets

| | | | | | | |
|---|---|---|---|---|---|---|
| acetone | 1.25 | 4.23 | 0.30 | 0.030 | 0.47 | 0.78 | note:
The sensor operating temperature is 340° C., $G_0$ is the base conductance, $\Delta G_{200}$ is the increase in conductance over this base for 200 ppm of gas (both in units of micromhos), slope is the log-log slope of conductance versus concentration.

TABLE 2

Examples of Selectivity of a Bismuth Molybdate Evaporated Film

| Reducing Gas | $G_0$ | $\Delta G_{200}$ |
|---|---|---|
| CO | 0.0319 | 0.007 |
| $H_2$ | 0.035 | 0.015 |
| $H_2S$ | 0.045 | 0.062[a] |
| Methane | 0.040 | — |
| Propane | 0.036 | 0.001 |
| Butane | 0.019 | 0.018 |
| N-Octane | 0.036 | 0.205[b] |
| Propene | 0.022 | 0.037 |
| Pentene | 0.017 | 0.102 |
| Methanol | 0.035 | 0.137 |
| Ethanol | 0.035 | 0.348 |
| 2-Propanol | 0.038 | 0.139 |
| 1-Butanol | 0.033 | 0.613 |
| Acetone | 0.041 | 0.114 |
| 3-Pentanone | 0.037 | 0.436[c] |

Note:
The sensor operating temperature is 340° C., $G_0$ is the base conductance, $\Delta G_{200}$ is the increase in conductance over this base for 200 ppm of gas (both units of micromhos). Exceptions are (a) 11 ppm, (b) 15 ppm, and (c) 100 ppm.

PREPARATION OF THE GAS SENSOR

Pellets of bismuth molybdate were prepared by co-precipitation from an aqueous solution of bismuth nitrate and ammonium heptamolybdate. The precipitated material was heated, to remove water, convert hydroxides to oxides, and induce sintering or even melting. Good sensitivity was obtained with pellets that were predominately alpha phase along with some gamma phase, as determined by X-ray diffraction. Example 1 describes a detailed preparation procedure for a bismuth molybdate co-precipitated powder and a pellet.

EXAMPLE 1

The two component solutions are first prepared 0.1 M ammonium molybdate (($NH_4)_6Mo_7O_{24}.4H_2O$) dissolved in 5% ammonium hydroxide ($NH_4OH$); and 0.5 M bismuth nitrate ($Bi(NO_3)_3.5H_2O$) in 5M nitric acid ($HNO_3$). The molybdate solution is then added dropwise to the bismuth solution while stirring until the desired proportions are obtained. The atomic Bi/Mo ratio was equal to 1. The resultant solution is co-precipitated by the slow (dropwise) addition of ammonium hydroxide. The precipitation is completed at about a pH of 6. After 16 hours the precipitate was filtered to remove excess solution and dried at 140° C. for 4 hours. A final calcining at 500° C. in air for about 2 hours was used to drive out ammonia and nitric oxide gases and produce the bismuth molybdate compound. The material is then ground to a fine powder and stored.

For the initial gas sensing studies pressed pellets were made of various bismuth molybdate powders. The pressure used was about $9 \times 10^8$ N/m$^2$ with a pellet size of 5 mm diameter and 1 mm thickness. It was found that the bismuth molybdate pellets formed were quite brittle and had a tendency to break. To improve their strength some of the pellets were sintered (in air) at temperatures just below their melting points which are for alpha 650° C., beta 662° C., and gamma 933° C.

Unlike prior art tin oxide gas sensors, bismuth molybdate sensors have proven to be equally effective or better when prepared as thin evaporated films. Studies were made to determine the optimum bismuth to molybdate ratio with respect to sensitivity for ethanol. Example 2 shows the detailed steps to produce an optimized evaporated layer of bismuth molybdate.

EXAMPLE 2

The bismuth molybdate powder of Example 1 was placed in a molybdenum boat in a standard vacuum evaporator. Current was applied to the boat, melting the powder and causing evaporation onto a fused quartz substrate. The evaporation was continued until a thin film monitor indicated 10,000 angstrom thickness. The films when first evaporated are black in colour due to the loss of oxygen as the bismuth molybdate decomposes and evaporates separately as bismuth and molybdenum oxides. The initial stoichiometry of the source powder was Mo/Bi=1(or 2/2). The film was then calcined at 400° C. for about three hours. This recovered the pale yellow colour of the catalyst and produced a stoichiometric (with respect to oxygen) mixture of phases of bismuth molybdate. The final phases obtained in the film of course depend on the initial phases evaporated. The actual phases obtained in Example 2 were an alpha plus gamma mixture as determined by X-ray diffraction.

Evaporated film sensors were prepared on a quartz substrate using bismuth molybdates in the bismuth to molydenum ratios ⅔, 2/2, and 2/1. Films prepared from the 2/2 mixture were the most sensitive to the presence of ethanol, films prepared from the 2/1 mixture showed some response to the presence of ethanol while the films prepared from the ⅔ ratio were almost totally insensitive.

Figure 1B:
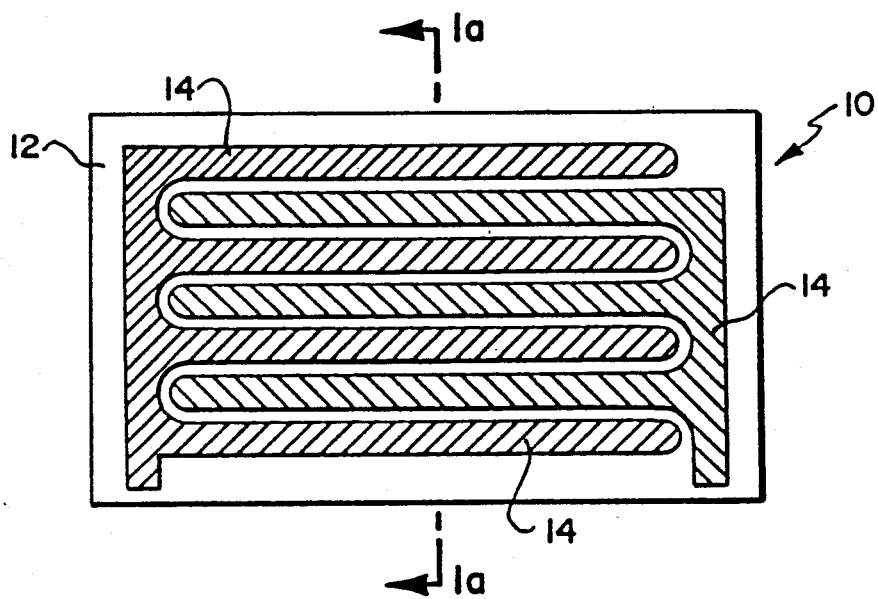

Bismuth molybdate films have been successfully evaporated onto a number of different substrates: ceramic, glass, fused quartz, and fused quartz annealed to remove excess water. In the example of FIGS. 1(a) and 1(b), the substrate was quartz. Gold electrical contacts were applied by evaporation in an interlocking finger pattern over the semiconductor on one end of a rectangularly shaped substrate. The sensor was tested in a small tube furnace.

Since resistance of a thin layer of bismuth molybdate is somewhat high compared to the resistance of a normal tin oxide sensor, efforts were made to lower this resistance to more satisfactory values. This was done by depositing inter-digitated gold contacts on a fused quartz substrate before evaporating the bismuth molybdate. FIGS. 1(a) and 1(b) show such an interdigitated structure 10 incorporating a quartz substrate 12, gold contacts 14 and bismuth molybdate 16 (the bismuth molybdate layer is not shown in FIG. 1(b), to avoid obscuring the contacts). As the resistance increases proportional to the distance between the contacts and decreases proportional to the length of the contacts it is clear that this construction will give a relatively low resistance.

Bismuth iron molybdate has been prepared by coprecipitation, subsequent calcining, followed by formation as a pressed pellet and further calcining. Example 3 describes a typical detailed preparation procedure.

EXAMPLE 3

Solutions of $(NH_4)_6Mo_7O_{24} \cdot 4H_2O$ in 5% $NH_4OH$, $Bi(NO_3)_3 \cdot 5H_2O$ in 30% $HNO_3$, and $Fe(NO_3)_3 \cdot 9H_2O$ in 30% $HNO_3$ were prepared in the molar proportions of Bi:Fe:Mo=3:1:2 and then mixed. The nitrates were mixed immediately and the ammonium heptamolybdate added drop by drop while stirring to prevent premature precipitation. Concentrated ammonium hydroxide solution was then added in a similarly careful manner until precipitation occurred at about a pH of 4 to 7. The solution was filtered and the precipitate dried on a glass petri dish at temperatures up to 300° C. to remove the water and to drive off ammonia and nitric oxides. The dry powder was then finely ground in a mortar, calcined at 400° C. for three hours, reground and stored. The final product was a brownish yellow in color.

The identification of the catalyst powder was confirmed by a standard powder X-ray diffraction technique using a computerized horizontal diffractometer and Cu K-alpha radiation. Powder calcined at 500° C. and above showed the X-ray peaks associated with an ordered scheelite structure. Those calcined at 400° C. showed the disordered structure.

Figure 1C:
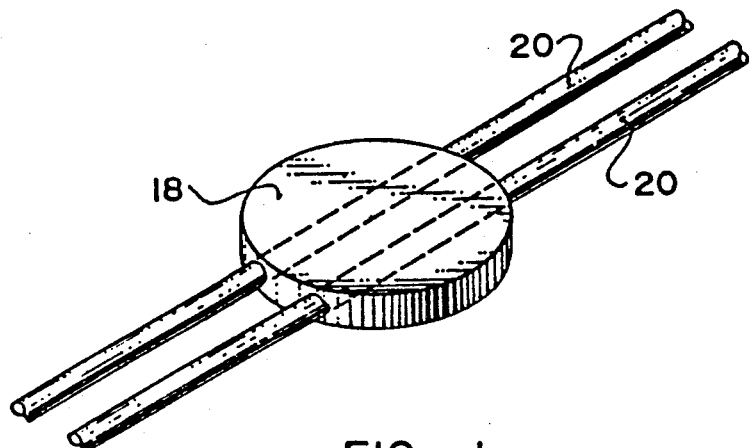
FIG. 1(c) is a pictorial illustration of a pressed pellet of bismuth molybdate (or bismuth iron molybdate) with embedded gold contacts.

The pellets used for gas sensing measurements were prepared using a specially designed press that allowed gold wires to be embedded. The pellets formed were 5 mm in diameter and about 1 mm thick. At the press induced pressure of about $5 \times 10^8$ N/m$^2$ the pellets reached a density of about 4 g/cm$^3$. This can be compared to the single crystal density of 7.16 5 g/cm$^3$. The wires, 0.12 mm in diameter, ran completely through the disk perpendicular to the vertical axis of the pellet disk, at a separation of 2 mm. FIG. 1(c) illustrates the pellet disk 18 with embedded wires 20. Before use, the pellet was again sintered (calcined) at 400° C., or at a higher temperature for some experiments.

To study the effect of additives, platinum black was mixed into the bismuth iron molybdate powder just before the final sintering. The percentages used by weight were 7 and 21 which showed much the same results. The platinum was well dispersed and active when the sintering temperature was 500° C. or above. The mixed powder was made into pellets for testing.

For the case of silver doping, 1% by weight of $AgNO_3$ was mixed with the bismuth iron molybdate powder in an aqueous slurry. The sample was then sintered at 500° C. and made into a pellet as before. As in all cases the pellets were re-sintered for added strength at the temperature being studied.

The pellet with attached wires was mounted on a quartz slide that allowed the pellet to sit vertically in a small tube furnace about 5 cm long and 5 cm in diameter. Contact to copper wires was made at the other end of the slide using silver dag as physical and electrical support, outside the furnace. A chromel alumel thermocouple in close proximity to the sensor was used to monitor and control the temperature (using standard electronics). This system was placed in a large plexiglass chamber to allow easy injection of known amounts of gas or solvent.

SENSOR RESPONSE

Figure 6B:
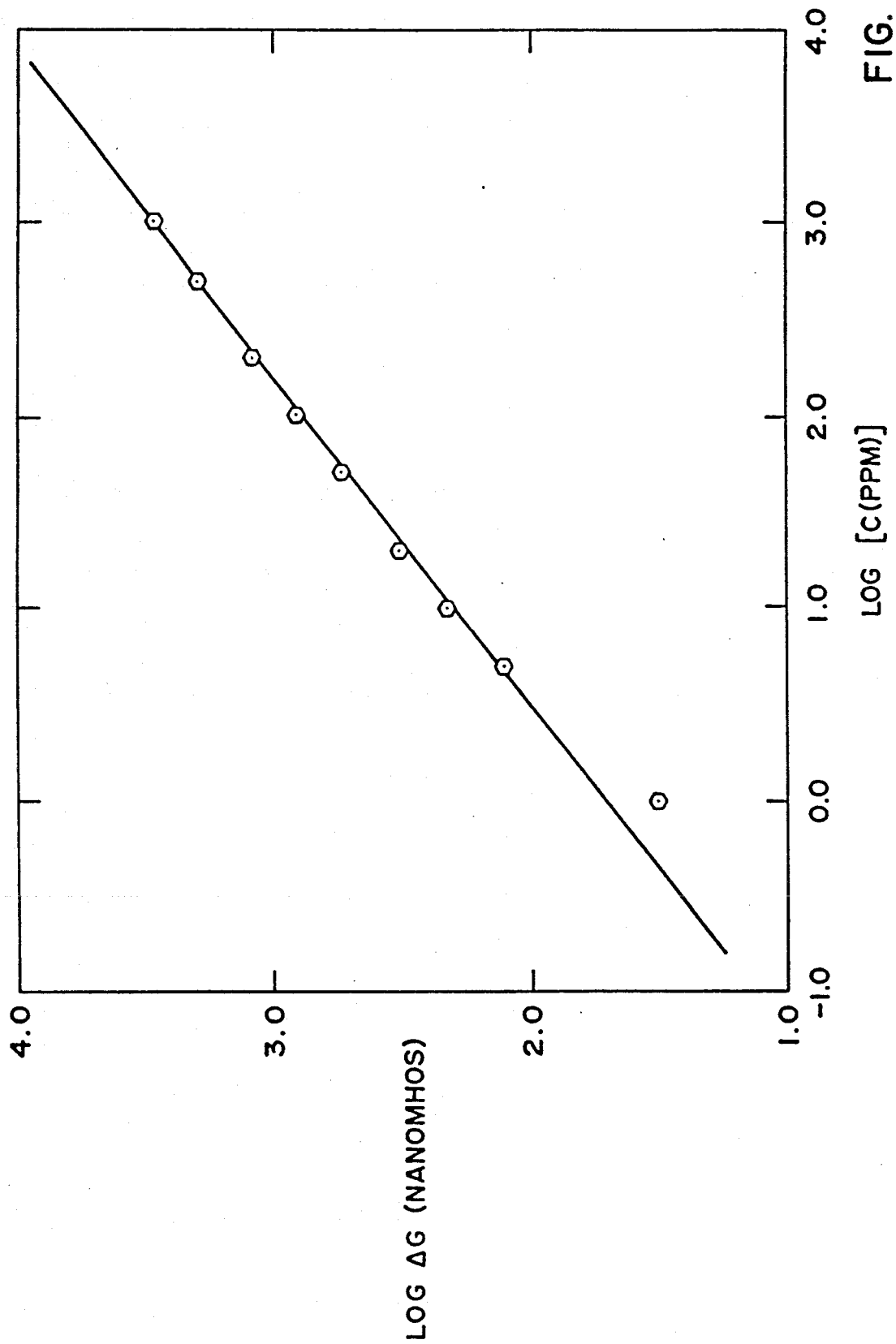
FIG. 6(b) plots the same data as FIG. 6(a), but with logarithmic nanomhos as the ordinate and logarithmic concentration as the abscissa.

FIGS. 2 and 6 and Tables 1 and 2 show the sensitivity of the sensors to various gases. More particularly, FIG. 2 plots gas concentration versus change in conductance for an evaporated film of bismuth molybdate upon exposure to eleven different reducing agents identified by letters "A" through "K" in FIG. 2 as follows; A: methane and propane; B: carbon monoxide; C: hydrogen; D: Iso-Octane; E: acetone; F: methanol; G: Iso-propanol; H: ethanol; I: 3-Pentanone; J: 1-butanol; and, K: N-Octane. FIG. 6(a) plots time versus conductance for a bismuth molybdate sensor exposed to eleven different concentrations of ethanol vapor identified on FIG. 6(a) with the letters "A" through "K" as follows. A: laboratory air ($G/G_o=1$); B: 1 ppm ethanol ($G/G_o=2.5$); C: 5 ppm ethanol ($G/G_o=7.0$); D: 10 ppm ethanol ($G/G_o=10.8$); E: 20 ppm ethanol ($G/G_o=16.0$); F: 50 ppm ethanol ($G/G_o=26.1$); G: 100 ppm ethanol ($G/G_o=38.4$); H: 200 ppm ethanol ($G/G_o=56.9$); I: 500 ppm ethanol ($G/G_o=93.6$); J: 1,000 ppm ethanol ($G/G_o=136.5$); and, K: venting. FIG. 6(b) plots the same data as FIG. 6(a) logarithmically, showing a power law dependence of 0.58. All of the films of bismuth molybdate were prepared in the manner described in Example 2. A very low sensitivity to short alkanes, CO and hydrogen, a medium sensitivity to longer alkanes and alkenes, and a high sensitivity for alcohols and ketones is observed.

With reference to FIG. 6, it should be noted that sensitivity to very small amounts of vapor (1 ppm EtOH) can be attained. This is greater than that seen for most semiconductor gas sensors, primarily because the baseline is stable against relative humidity.

For the case of Platinum doped bismuth iron molybdate, ratios up to 100 times the baseline can be seen for injection of 200 ppm EtOH. The use of silver dopant allows the detection of hydrogen. Similar effects are expected with palladium dopant.

Figure 3:
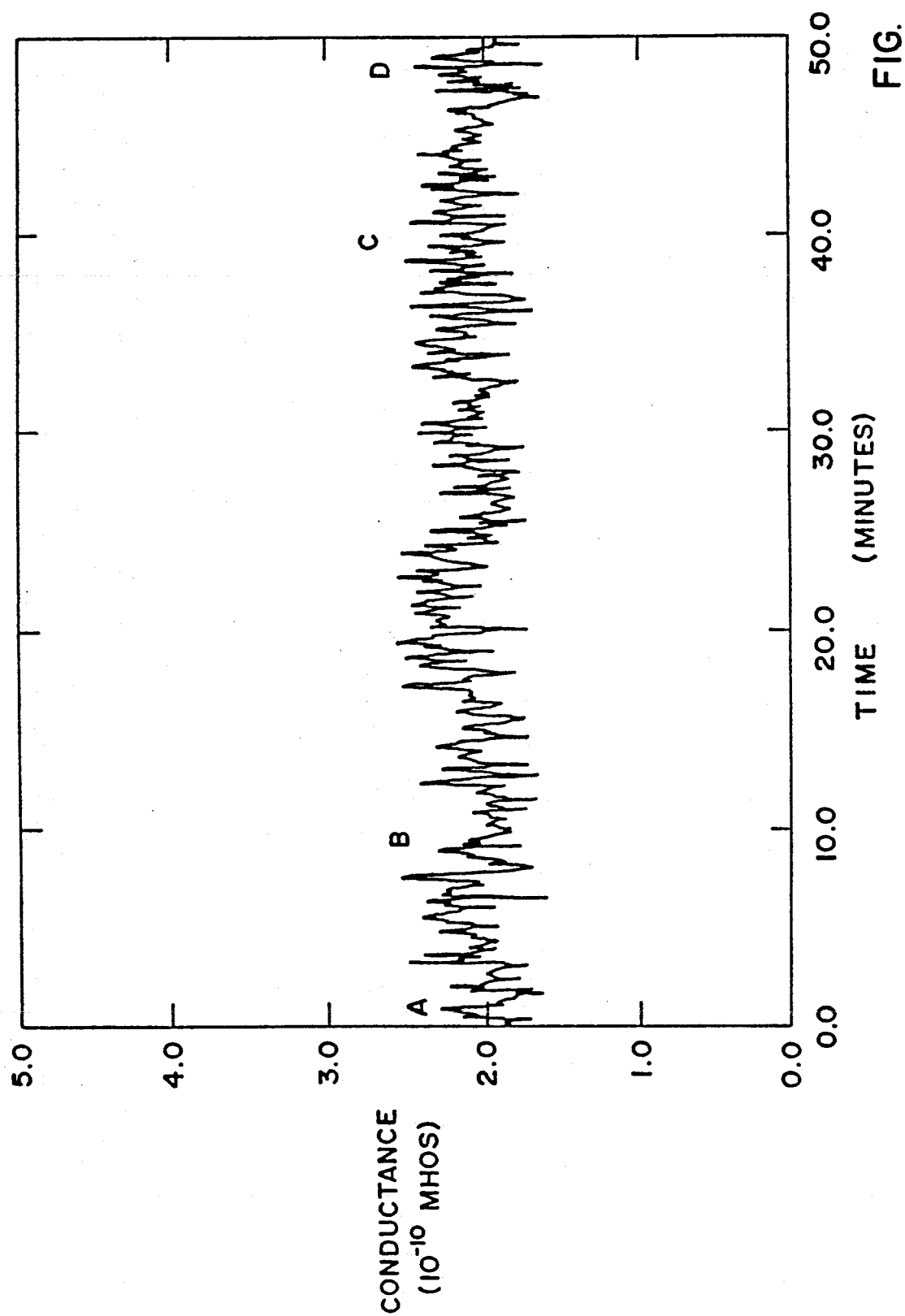
FIG. 3 is a graph on which time (in minutes) is plotted as the abscissa, versus conductance (in $10^{-10}$ mhos) as the ordinate for a sensor constructed in accordance with the invention and exposed to air of progressively increasing relative humidity.

FIG. 3 illustrates the sensor's lack of sensitivity to relative humidity, showing that the base line itself hardly changes with relative humidity. More particularly, FIG. 3 plots conductance versus time for a bismuth molybdate evaporated film sensor operated in an atmosphere of progressively increasing relative humidity; regions "A", "B", "C" and "D" on FIG. 3 respectively denoting atmospheres of 40%, 54%, 66% and 77% relative humidity. It has been found there is also no synergistic effect on the conductivity in an ethanol vapor atmosphere.

Figure 4A:
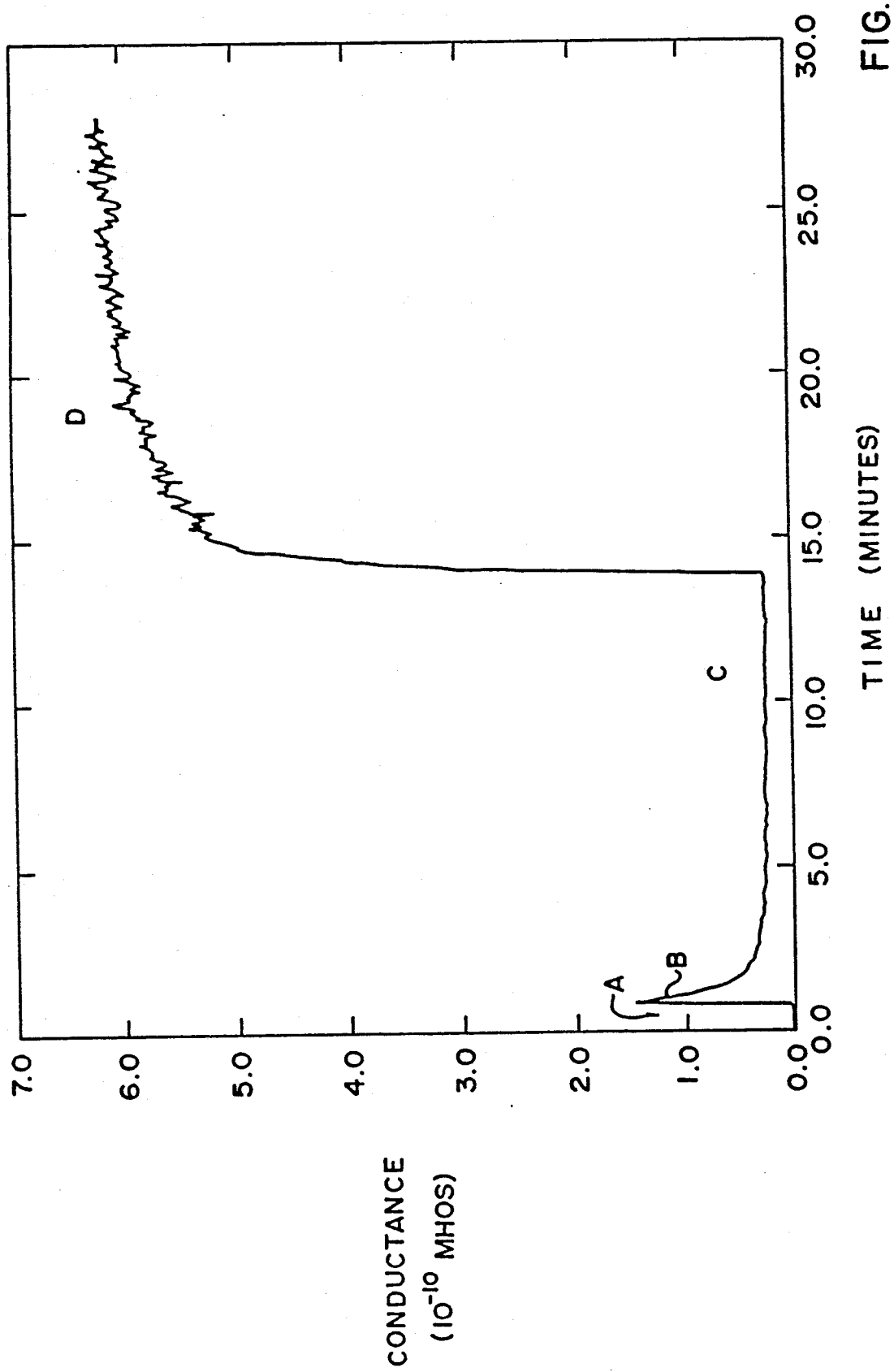
FIG. 4(a) is a graph on which time (in minutes) is plotted as the abscissa, versus conductance (in $10^{-8}$ mhos) as the ordinate for a sensor constructed in accordance with the invention, and exposed to a 200 ppm concentration of ethanol vapor to show the sensor's short turn on time.
Figure 4B:
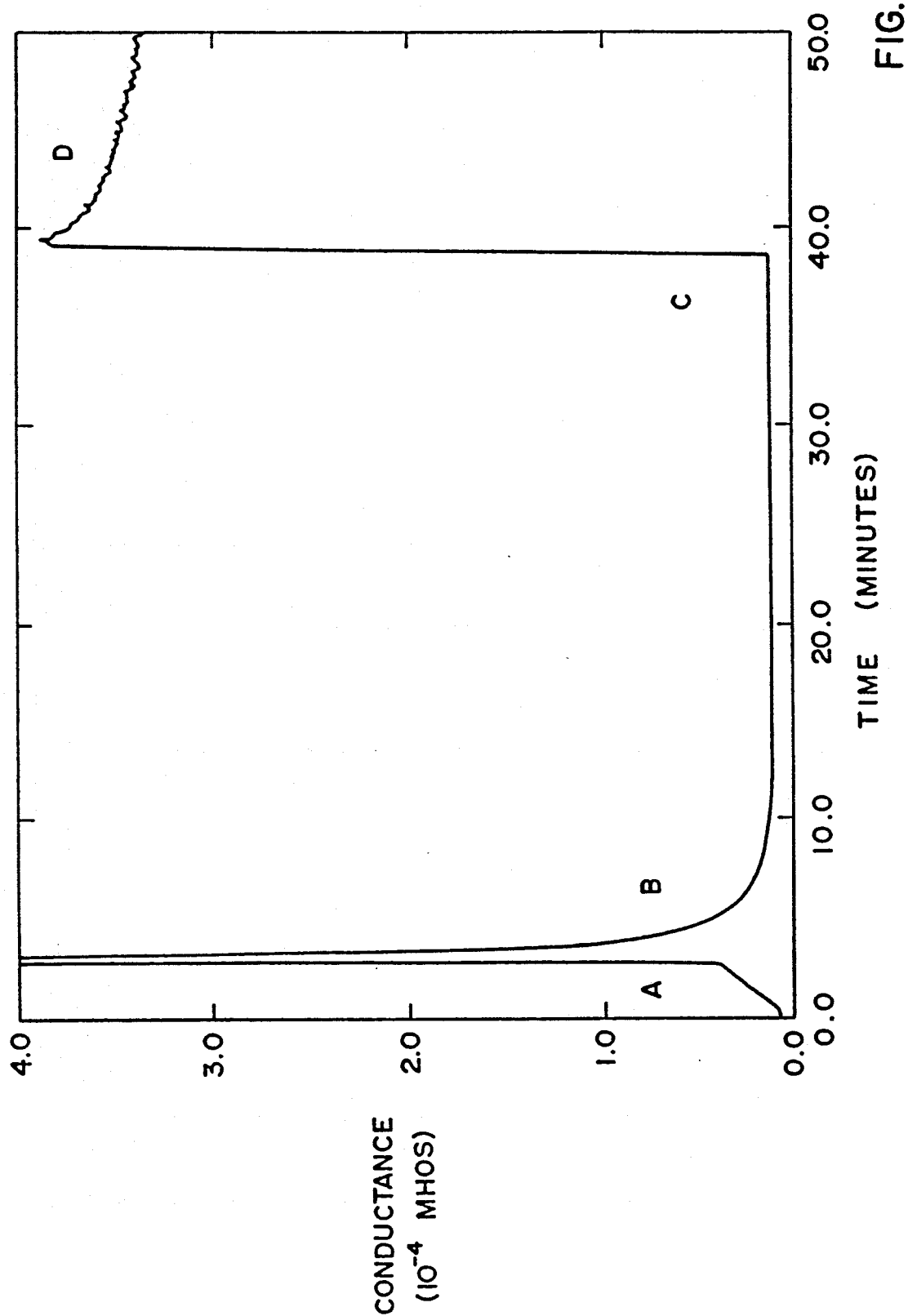
FIG. 4(b) shows the turn on time of a similarly operated prior art tin oxide sensor, with conductance (in $10^{-4}$ mhos) plotted as the ordinate.

FIGS. 4(a) and (b) show the substantial improvement in turn-on time for a sensor constructed in accordance with the invention, as compared with a typical prior art (Figaro TGS#812) tin oxide gas sensor measured under the same conditions, except the waiting time before ethanol injection was of necessity longer. With reference to FIG. 4(a), region "A" shows the response characteristic of a bismuth molybdate sensor constructed in accordance with the invention without power having been applied thereto for one day; region "B" shows the response transient observed when power is initially applied to the sensor; region "C" shows the attainment of steady state operation; and, region "D" is the response obtained upon exposure of the sensor to a 200 ppm concentration of ethanol. The same regions are labelled on FIG. 4(b), which depicts the response of the prior art sensor under similar operation. As FIG. 4(b) shows, after the heater the prior art device has been turned off for some time, one has to wait some minutes for the SnO2-based to come to eguilibrium—a process presumably with burning of organics that have been depos on the gas sensor during the interim. The bismuth gas sensor, on the other hand, shows only a (and much shorter) transient response so can use test for 200 ppm alcohol immediately after g- it on. This makes the sensor much more practical use for testing of breath, for example, because t long wait time is not necessary.

There is also a difference in long term transients. The bismuth molybdate come to final equilibrium in about ten minutes whereas the SnO2-based sensors require days "burn in" after they are made.

Figure 5:
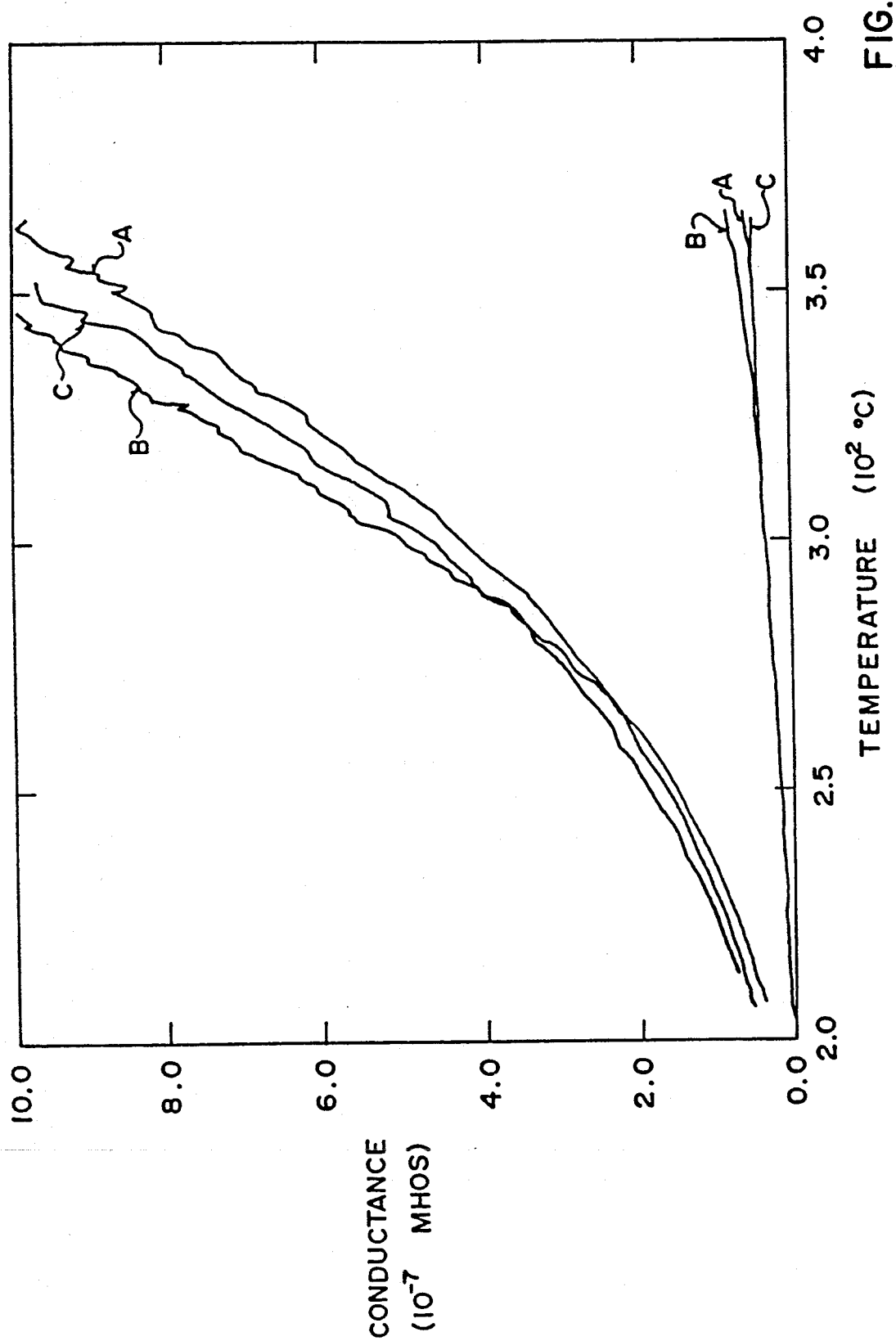
FIG. 5 is a graph on which temperature (in hundreds of degrees Celsius) is plotted as the abscissa, versus conductance (in $10^{-7}$ mhos) for three different bismuth molybdate sensors constructed in accordance with the invention.

FIG. 5 shows the stability of a bismuth molybdate sensor constructed in accordance with the invention, while under continuous use. The three lower curves on FIG. 5 depict the sensor's response when operated in the presence of air; the three upper curves depict the sensor's response when operated in the presence of a 200 ppm of ethanol vapor. The curves labelled denote an initial test of the sensor; the curves label "B" show the sensor after one month of continuous operation; and, the curves labelled "C" show the sensor two months of continuous operation. It can be seen there is very little change in response over two month period. The change that is seen may be due errors in temperature calibration rather than in sensor response. Similar stability has been observed for bismuth iron molybdate pellets.

Figure 7:
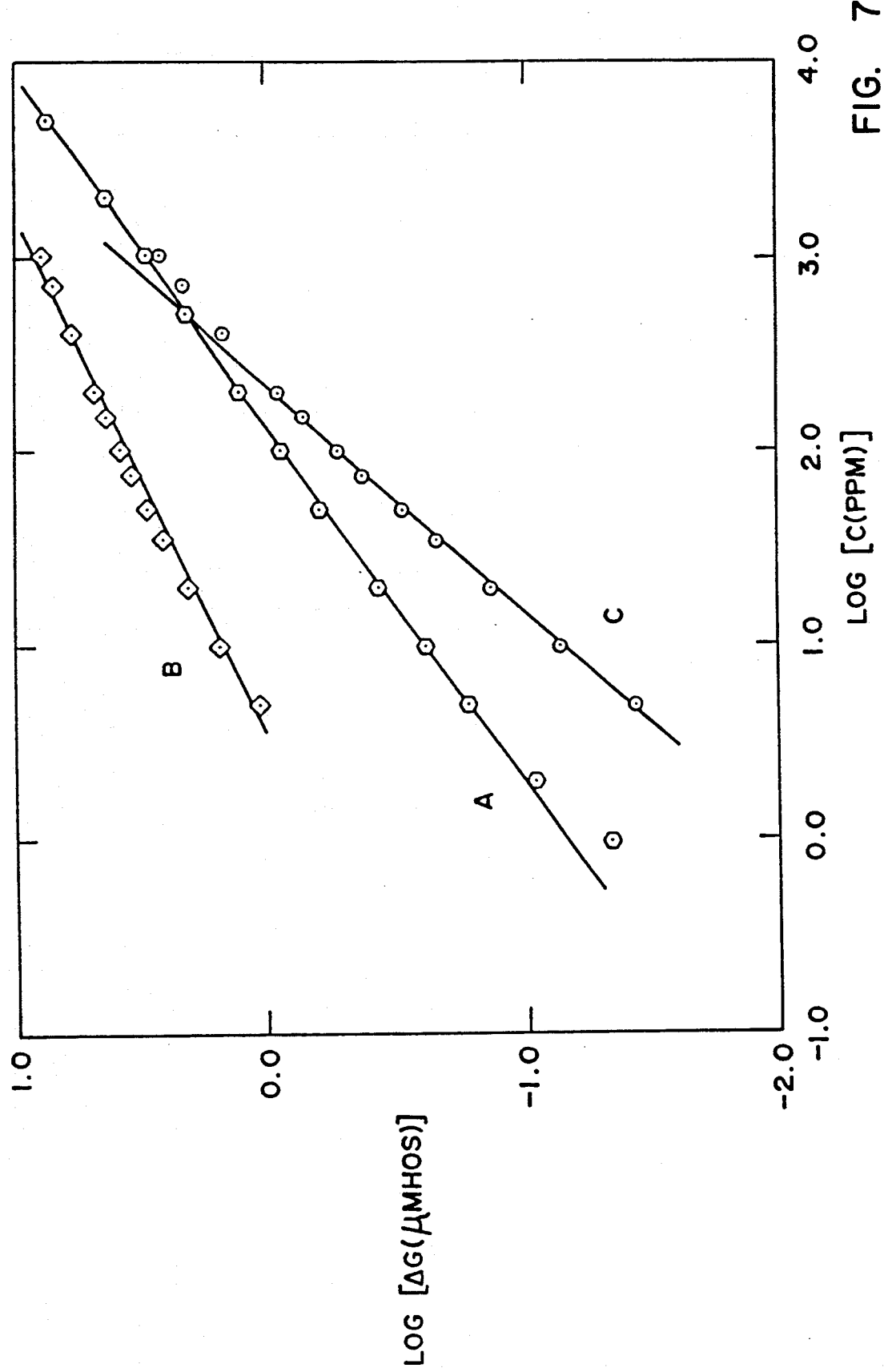
FIG. 7 is graph on which logarithmic concentration (in parts per million) is plotted as the abscissa, versus logarithmic change in conductance (in micromhos) for three bismuth iron molybdate sensors constructed in accordance with the invention and operated at 340° C. in the presence of various concentrations of ethanol vapor.

FIG. 7 shows the effect on sensor response linearity of different preparation techniques of bismuth iron molybdate pellets. More particularly, the lines labelled "A", "B", and "C" on 7 respectively designate the operating characteristics of pellets sintered at 400° C. (line "A"), at 500° C. (line "B"), and at 500° C. with 21% platinum (line "C"). The sensors were each operated at 34° C. and exposed to varying concentrations of ethan obtain the data plotted in FIG. 7. For platinum doped material (i.e. the line labelled "C" in FIG. 7) the conductivity measured is close to being a direct function of the concentration of reducing vapor. This would simplify calibration in a practical device as well as extend the range of useful sensor operation.

Figure 8:
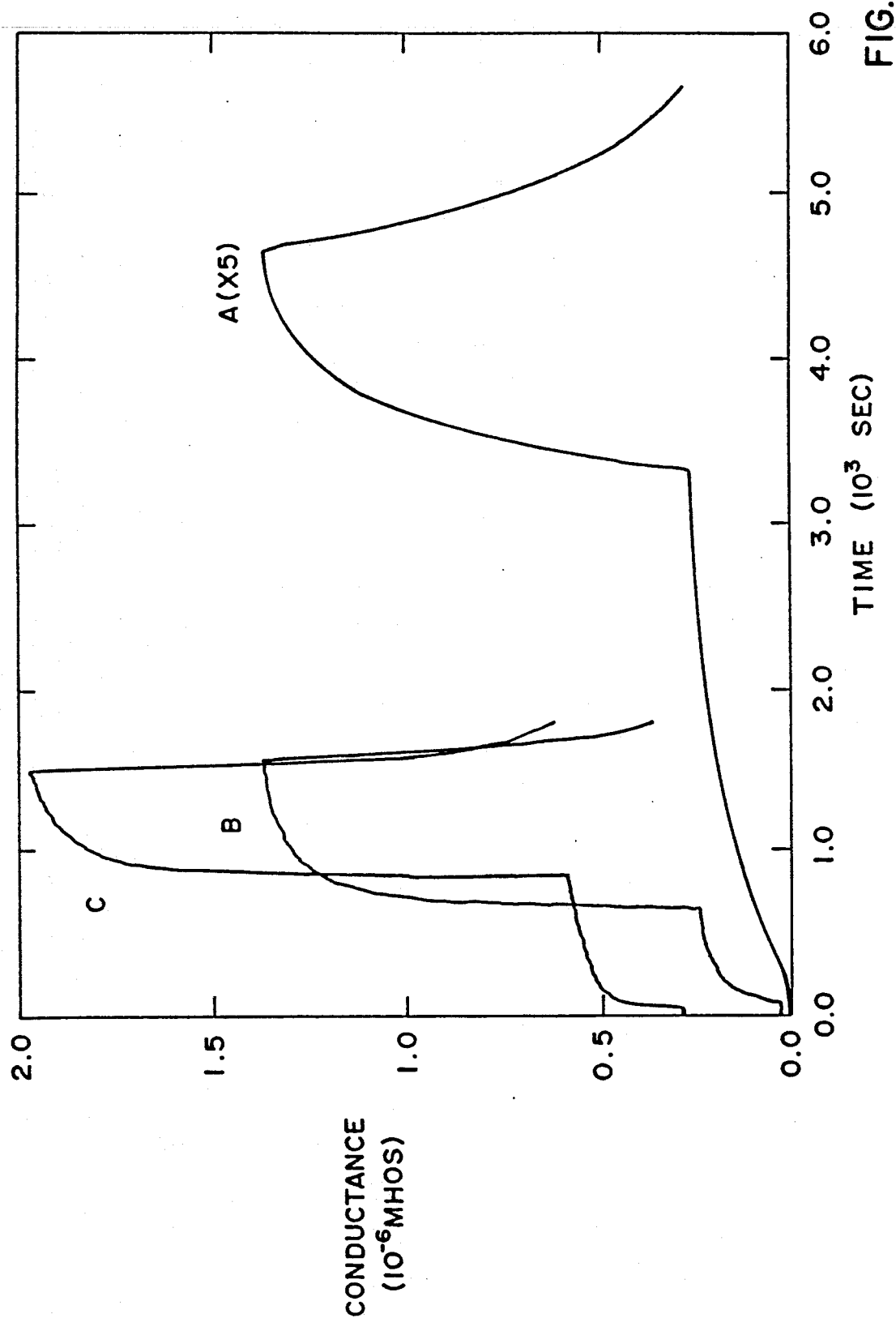
FIG. 8 is a graph on which time (in thousands of seconds) is plotted as the abscissa, versus conductance (in $10^{-6}$ mhos) as the ordinate for a bismuth iron molybdate sensor constructed in accordance with the invention.

FIG. 8 shows the e of operating temperature on the speed of response of a bismuth iron molybdate pellet sensor. More particularly, FIG. 8 plots as curves "A", "B" and "C" respectively, the operating characteristics of a 7% platinum doped bismuth iron molybdate sensor (prepared by sintering at 500° C.) after exposure to 20 ppm ethanpl, followed by exposure to 200 ppm ethanol; curve "A" showing operation at 220° C. (magnified by a factor of five to improve clarity), curve "B" showing operation at 330° C. and curve "C" showing operation at 410° C. change in vacancy mobility are believed to be responsible to the variation of response speed with temperature. At 220° C. the sensor responds slowly but shows great (a factor of about 400 change in conductivity for 200 ppm EtOH). At 410° C. the sensor is much faster but has lost sensitivity (a factor of 7). 330° C. is considered by the inventors to be a compromise temperature (a factor of about 40).

As will be apparent those skilled in the art in the light of the disclosure many alterations and modifications are without departing from the spirit of scope thereof. Accordingly, the scope of the invention is to be construed in accordance with the substance defined by following claims.

We claim:

1. A gas sensor, comprising:
   (a) a substrate;
   (b) a film mixture of the $Bi_2Mo_3O_{12}$ and $Bi_2MoO_6$ phases of bismuth molybdate deposited on said substrate; and,
   (c) means for electrically coupling said thin film to a monitor circuit for monitoring the electrical resistivity of said thin film during exposure of said thin film to a selected gas.

2. A gas sensor, comprising:
   (a) a film composition of bismuth iron molybdate; and,
   (b) means for electrically coupling said composition to a monitor circuit for monitoring the electrical resistivity of said composition during exposure of said composition to a selected gas.

3. A gas sensor as defined in claim 2, wherein said bismuth iron molybdate is doped with a metal selected from the group consisting of platinum, silver and palladium.

4. An alcohol gas sensor, comprising:
   (a) a substrate;
   (b) a film mixture of the $Bi_2Mo_3O_{12}$ and $Bi_2MoO_6$ phases of bismuth molybdate deposited on said substrate; and,
   (c) means for electrically coupling said thin film to a monitor circuit for monitoring the electrical resistivity of said thin film during exposure of said thin film to a selected gas.

5. An alcohol gas sensor, comprising:
   (a) a film composition of bismuth iron molybdate; and,
   (b) means for electrically coupling said composition to a monitor circuit for monitoring the electrical resistivity of said composition during exposure of said composition to a selected gas.

6. An alcohol gas sensor as defined in claim 5, wherein said bismuth iron molybdate is doped with a noble metal selected from the group consisting of platimun, silver and palladium.

7. A gas sensor for detecting, in a selected gas, the presence of a gas selected from the group consisting of alcohols, ketones, alkenes, and long chain alkanes, said gas sensor comprising:
   (a) a substrate;
   (b) a film mixture of the $Bi_2Mo_3O_{12}$ and $Bi_2MoO_6$ phases of bismuth molybdate deposited on said substrate; and,
   (c) means for electrically coupling said thin film to a monitor circuit for monitoring the electrical resistivity of said thin film during exposure of said thin film to said selected gas.

8. A gas sensor for detecting, in a selected gas, the presence of a gas selected from the group consisting of alcohols, ketones, alkenes, and long chain alkanes, said gas sensor comprising:
   (a) a film composition of bismuth iron molybdate; and,
   (b) means for electrically coupling said composition to a monitor circuit for monitoring the electrical resistivity of said composition during exposure of said composition to said selected gas.

9. A gas sensor as defined in claim 8, wherein said bismuth iron molybdate is doped with a metal selected from the group consisting of platinum, silver and palladium.

10. A method of measuring gas concentration, comprising the steps of:

(a) exposing said gas to a sensor comprising a mixture of the $Bi_2Mo_3O_{12}$ and $Bi_2MoO_6$ phases of bismuth molybdate; and (b) measuring the electrical resistance of said sensor.

11. A method as defined in claim 10 further comprising heating said sensor to an operating temperature of about 340 degrees celsius.

12. A method of measuring gas concentration, comprising the steps of:

(a) exposing said gas to a sensor comprising bismuth iron molybdate; and (b) measuring the electrical resistance of said sensor.

13. A method as defined in claim 12 further comprising heating said sensor to an operating temperature of about 340 degrees celsius.

* * * * *